(12) United States Patent
Miki et al.

(10) Patent No.: US 6,664,430 B1
(45) Date of Patent: Dec. 16, 2003

(54) CATALYSTS FOR THE PREPARATION OF FLUORINATED ALCOHOLS AND PROCESS FOR THE PREPARATION OF FLUORINATED ALCOHOLS

(75) Inventors: Jun Miki, Settsu (JP); Hirokazu Aoyama, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/959,942

(22) PCT Filed: Apr. 25, 2000

(86) PCT No.: PCT/JP00/02711

§ 371 (c)(1),
(2), (4) Date: Nov. 13, 2001

(87) PCT Pub. No.: WO00/69557

PCT Pub. Date: Nov. 23, 2000

(30) Foreign Application Priority Data

May 12, 1999 (JP) ............................................ 11-131362
Aug. 9, 1999 (JP) ............................................ 11-225112

(51) Int. Cl.$^7$ ......................... C07C 31/34; C07C 27/10; B01J 31/00
(52) U.S. Cl. ....................... 568/842; 568/844; 568/910; 502/102; 502/120
(58) Field of Search .............................. 568/842, 844, 568/910; 502/102, 120

(56) References Cited

U.S. PATENT DOCUMENTS 4,748,282 A * 5/1988 Bargigia et al.
5,489,722 A * 2/1996 Resasco et al.

FOREIGN PATENT DOCUMENTS

| EP | 0 247 614 | 12/1987 |
| JP | 63-270633 | 11/1988 |
| JP | 6-184025 | 7/1994 |

* cited by examiner

*Primary Examiner*—Samuel Barts
*Assistant Examiner*—Sikarl A. Witherspoon
(74) *Attorney, Agent, or Firm*—Larson & Taylor PLC

(57) ABSTRACT

The present invention provides a catalyst for preparing a fluorine-containing alcohol compound, the catalyst having at least one component selected from elements in Group 1B, Group 2B, Group 6A, Group 7A and Group 8 of the periodic table, ions of these elements, oxides containing these elements, hydroxides containing these elements and salts containing these elements, said component being supported on at least one complex oxide selected from Si—Al complex oxides, Al—P complex oxides and Si—Al—P complex oxides; and a method for preparing a fluorine-containing alcohol compound, the method comprising reacting a halogenated fluorine compound with water in the presence of the catalyst.

According to the present invention, a fluorine-containing alcohol compound can be prepared at a relatively low reaction temperature and in a high yield.

4 Claims, No Drawings

CATALYSTS FOR THE PREPARATION OF FLUORINATED ALCOHOLS AND PROCESS FOR THE PREPARATION OF FLUORINATED ALCOHOLS

TECHNICAL FIELD

The present invention relates to a method for preparing a fluorine-containing alcohol compound and a catalyst used in the preparation method.

BACKGROUND ART

Japanese Unexamined Patent Publication No. 1992-506507 suggests a method for preparing a fluorine-containing alcohol having water repellency and oil repellency by treating a halogenated alkyl on a catalyst to convert it into an alcohol. However, this method has the shortcomings of using a gas phase reaction at a temperature as high as 400 to 600° C. and of a low degree of conversion and selectivity.

DISCLOSURE OF INVENTION

A primary object of the present invention is to provide a method for preparing a fluorine-containing alcohol compound without using unusual reagents or solvents under relatively moderate reaction conditions and in a high yield.

The inventors of the present invention conducted extensive research to achieve the above object. Consequently, they found that a fluorine-containing alcohol compound can be prepared at a relatively low reaction temperature and in a high yield by using a catalyst which has an element of a specific group of the periodic table, an ion of such an element, an oxide, hydroxide, salt or the like containing such element(s) supported on a specific complex oxide. The present invention was accomplished based on this finding.

Specifically, the present invention provides the following catalyst for preparing a fluorine-containing alcohol compound and a method for preparing a fluorine-containing alcohol compound.

1. A catalyst for preparing a fluorine-containing alcohol compound, the catalyst having at least one component selected from
   (i) at least one element selected from the elements in Group 1B, Group 2B, Group 6A, Group 7A and Group 8 of the periodic table,
   (ii) at least one ion of the element of the above (i),
   (iii) at least one oxide containing one or more elements of the above (i),
   (iv) at least one hydroxide containing one or more elements of the above (i), and
   (v) at least one salt containing one or more elements of the above (i),
   said component being supported on at least one complex oxide selected from Si—Al complex oxides, Al—P complex oxides and Si—Al—P complex oxides.
2. The catalyst according to item 1 in which the complex oxide is an oxide having a zeolite structure.
3. The catalyst according to item 1 or 2, wherein the component supported on the complex oxide is at least one component selected from ions of elements selected from Cu, Ag, Ni, Co, Fe, Hg and Pd, oxides containing such element(s), hydroxides containing such element(s) and salts containing such element(s).
4. A method for preparing a fluorine-containing alcohol compound represented by formula (II):

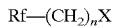
$$Rf—(CH_2)_n OH \quad (II)$$

wherein Rf represents a perfluoroalkyl group or a polyfluoroalkyl group and n is an integer from 1 to 5, the method comprising the step of reacting water with a halogenated fluorine compound represented by formula (I):

$$Rf—(CH_2)_n X \quad (I)$$

wherein Rf is as defined in the above, X represents I, Br or Cl and n is as defined in the above, in the presence of the catalyst as defined in any one of the above items 1 to 3.

5. The method according to item 4, wherein the reaction between the halogenated fluorine compound and water is carried out in an atmosphere of an oxygen-containing gas.
6. The method according to item 4 or 5, wherein the reaction is carried out under increased pressure.
7. The method for preparing a fluorine-containing alcohol compound according to item 5, wherein X in formula (I) is I, the method further comprising the step of recovering $I_2$ produced as a byproduct.

The catalyst for preparing a fluorine-containing alcohol compound for use in the present invention has at least one component selected from
   (i) at least one element selected from the elements in Group 1B, Group 2B, Group 6A, Group 7A and Group 8 of the periodic table,
   (ii) at least one ion of the element of the above (i),
   (iii) at least one oxide containing one or more elements of the above (i),
   (iv) at least one hydroxide containing one or more elements of the above (i), and
   (v) at least one salt containing one or more elements of the above (i),
   said component being supported on at least one complex oxide selected from Si—Al complex oxides, Al—P complex oxides and Si—Al—P complex oxides.

Among these elements, examples of the elements in Group 1B include Cu, Ag and Au, among others; examples of the elements in Group 2B include Zn, Cd and Hg, among others; examples of the elements in Group 6A include Cr, Mo and W, among others; examples of the elements in Group 7A include Mn, Tc and Re, among others; examples of the elements in Group 8 include Ni, Co, Fe, Ru, Rh, Pd, Pt and Ir, among others. These elements may be used singly or in combinations of two or more species.

In the present invention, these elements may be supported, and the ions of these elements, oxides, hydroxides, salts or the like containing one or more of these elements may be also supported. Hereinafter in the present specification, these components may be collectively referred to as active components.

Among the active components, the oxides may be those containing one or more of the above elements, and the valence of the element is not restricted. The hydroxides may be those containing one or more of the above elements, and the valence of the element is not restricted. The ions may be those of the above elements, and the charge number of the ion is not restricted. Examples of the useful salts include sulfates, nitrates, carbonates and the like.

The above-mentioned active components may be used singly or in combinations of two or more species.

Among the above-mentioned active components, preferable are ions of Cu, Ag, Ni, Co, Fe, Hg, Pd and other elements, oxides containing one or more of these elements, hydroxides containing one or more of these elements, salts containing one or more of these elements, etc. The catalyst which uses the active component containing Cu, Ni or the like has high selectivity for the desired product; the catalyst using active component containing Ag allows a reaction at a relatively low temperature; and the catalyst using active component containing Fe exhibits good catalytic activity.

The catalyst of the present invention uses at least one complex oxide selected from Si—Al complex oxides, Al—P complex oxides and Si—Al—P complex oxides as a carrier to support the above-mentioned active component.

Examples of such complex oxides include silica-alumina, synthetic silica-alumina zeolite, natural silica-alumina zeolite, aluminum phosphate, synthetic aluminum phosphate zeolite, synthetic Si—Al—P zeolite (SAPO) and the like.

Using a catalyst having the above-mentioned component supported on at least one complex oxide selected from Si—Al complex oxides, Al—P complex oxides and Si—Al—P complex oxides can improve the degree of conversion of raw material, selectivity of the desired product, etc. in the below-mentioned method for preparing a fluorine-containing alcohol compound. Among these complex oxides, using an oxide having a zeolite structure particularly increases selectivity of alcohol.

The method to support the above active component on the complex oxide is not particularly limited, and may be suitably selected from various conventional support methods depending on the kind of the component to be supported. For example, the sol-gel method, hydrothermal synthesis, impregnation method, co-precipitation method, CVD method (chemical vapor deposition method), ion-implantation method or any other methods may be employed.

For instance, when using SAPO-11 zeolite as a Si—Al—P complex oxide, the above-mentioned active component can be supported on the complex oxide by immersing the zeolite in a solution of a soluble metal compound (e.g., an aqueous solution of copper sulfate or like metal salt) to impregnate the zeolite with the solution, optionally followed by heating. The forms of the complex oxide when immersed in a metal compound solution include, but are not limited to, powders, granules, tablets, honeycombs, among others.

In a catalyst comprising a complex oxide which has the above component supported thereon, the amount of the active component, calculated as the metal oxide, per the total catalyst is suitably about 1 to 30% by weight, preferably about 5 to 15% by weight.

Next, the method for preparing a fluorine-containing alcohol compound using the above-mentioned catalyst will be explained.

In the method of the present invention, in the presence of the above-mentioned catalyst, a fluorine-containing alcohol compound represented by formula (II)

Rf—(CH$_2$)$_n$OH     (II)

wherein Rf represents a perfluoroalkyl group or a polyfluoroalkyl group and n is an integer from 1 to 5 can be prepared by reacting water with a halogenated fluorine compound represented by formula (I):

Rf—(CH$_2$)$_n$X     (I)

wherein Rf and n are as defined above and X represents I, Br or Cl.

In the compound of formula (I), examples of the perfluoroalkyl group represented by Rf include $C_1$–$C_{20}$ straight-chain or branched-chain perfluoroalkyl groups. Specific examples include $CF_3$, $C_2F_5$, (n- or iso)$C_3F_7$, (n-, iso, sec- or tert-)$C_4F_9$, $CF_3(CF_2)_{m-}$ (m is an integer from 4 to 19), among others.

Examples of the polyfluoroalkyl group include $HCF_2(CF_2)_{p-}$ (p is an integer from 1 to 19), among others.

The reaction between the halogenated fluorine compound represented by formula (I) and water can be carried out by a batch method or a continuous method. The reactor for this reaction is not particularly restricted, and a gas phase continuous reactor equipped with reaction vessel such as fixed bed, fluidized bed, moving bed, etc., or a batch reactor may be used.

The method for reacting the halogenated fluorine compound and water by gas phase continuous reaction comprises, for example, the steps of placing a stainless-steel reaction tube filled with the catalyst of the present invention in an electric heating furnace, heating the catalyst layer to a reaction temperature, introducing the raw material and water into a vaporizer at a constant rate using a plunger pump or the like, conveying the vaporized gas to the catalyst layer by air or like carrier gases to react the vaporized gas, and recovering a reaction product with a subsequent trap or the like. Although favorable reaction conditions may somewhat vary depending on the kind of catalyst used, the reaction temperature may be about 120° C. to 400° C., preferably about 150° C. to 300° C. The reaction can be carried out under atmospheric pressure or increased pressure. Particularly, when reacting under increased pressure, preferably under absolute pressure of 0.294 MPa or higher, more preferably 0.392 MPa or higher, even more preferably 0.49 MPa or higher, particularly preferably 0.588 Mpa or higher, alcohol selectivity can be increased. The molar ratio of the halogenated fluorine compound to water is desirably about 1:0.2–1:200. W/F (contact time) may be about 0.1 to 10 g·sec/ml.

When the reaction is conducted by the batch method, it can be conducted, for example, by the method comprising the following steps: placing the raw material, water and the catalyst in an autoclave or like pressure vessel; and heating the mixture with a heater to a reaction temperature to allow the mixture to react for a certain period of time with stirring. Although preferable reaction conditions may somewhat vary depending on the kind of catalyst used, the reaction temperature may be about 120° C. to 400° C., preferably about 150° C. to 300° C. The molar ratio of the halogenated fluorine compound to water is desirably about 1:0.2–1:200. The weight ratio of the halogenated fluorine compound to the catalyst may be about 1:0.01–1:1. The reaction time may be about an hour to 100 hours.

As for the reaction atmosphere, the reaction may be conducted in an atmosphere including nitrogen, helium, carbon dioxide or like inert gases, air or like oxygen-containing gases, oxygen-containing gas diluted with an inert gas, among others. In particular, conducting reaction in an atmosphere of air or like oxygen-containing gas accelerates the oxidation of HX formed by the reaction and formation of $X_2$, thereby facilitating the recovery of $X_2$. The recovered $X_2$ is useful as a raw material in the production process of the starting compound represented by the above formula (I): Rf—(CH$_2$)$_n$X. Particularly when the formed $X_2$ is $I_2$, iodine can be advantageously recovered without troublesome and environmentally unfavorable treatments such as oxidation by chlorine which is conventionally necessary for recovering iodine from a waste liquid containing iodide ions. The thus recovered iodine is a very important resource which can be collected by distillation, sublimation or other methods. Such iodine can be used as a raw material for preparing the staring compound for use in the method of the present invention, i.e., halogenated fluorine compound.

In the continuous reaction, the supply of air and like oxygen-containing gas together with the raw material and water can prevent catalyst activity from decreasing. In this case, the amount of oxygen is preferably at least about ¼ mole per mole of the halogenated fluorine compound.

According to the preparation method of the present invention, by reacting water and the halogenated fluorine compound in the presence of the specific catalyst, the fluorine-containing alcohol compound can be prepared at a relatively low reaction temperature and in a high yield.

BEST MODE FOR CARRYING OUT THE INVENTION

Below, the present invention is explained in further detail with Examples. However, the present invention is not limited to these Examples.

Preparation of catalyst

PREPARATION EXAMPLE 1

$CuSO_4 \cdot 5H_2O$ (1.88 g) was dissolved in 30 cc of an ion exchange water, giving a aqueous solution of copper sulfate. 10 g of a commercially available Si—Al—P zeolite (SAPO-11) was added to 30 cc of this aqueous solution of copper sulfate to impregnate the zeolite with the aqueous solution of copper sulfate. This solution was filtrated, and then the collected product was dried and solidified with heating using a hot water bath.

Subsequently, the dried product was heated in a muffle furnace at 300° C. for 3 hours to subject to the reaction described in the below Examples. The heated product had 6% by weight of a supported copper compound, calculated as CuO.

PREPARATION EXAMPLE 2

A commercially available Si—Al—P zeolite (10 g) (SAPO-34) was added to 30 cc of the same aqueous solution of copper sulfate as that used in Preparation Example 1 to impregnate the zeolite with the aqueous solution of copper sulfate. This solution was filtrated, and then the collected product was dried and solidified with heating using a hot water bath.

Further, the dried product was heated in a muffle furnace at 300° C. for 3 hours to subject to the reactions as described below in Examples. The heated product had 6% by weight, calculated as CuO, of a supported copper compound.

PREPARATION EXAMPLE 3

$NiSO_4 \cdot 6H_2O$ (2.10 g) was dissolved in 30 cc of an ion exchange water, giving an aqueous solution of nickel sulfate. 10 g of a commercially available Si—Al—P zeolite (SAPO-34) was added to 30 cc of this aqueous solution of nickel sulfate to impregnate the zeolite with the aqueous solution of nickel sulfate. This solution was filtrated, and then the collected product was dried and solidified with heating using a hot water bath.

Further, the dried product was heated in a muffle furnace at 300° C. for 3 hours to subject to the reactions as described below in Examples. The heated product had 6% by weight, calculated as NiO, of a supported nickel compound.

PREPARATION EXAMPLE 4

$Fe_2(SO_4)3 \cdot nH_2O$ (1.30 g) (content: 60% by weight as $Fe_2(SO_4)_3$) was dissolved in 30 cc of an ion exchange water, giving an aqueous solution of ferric sulfate. 10 g of a commercially available Si—Al—P zeolite (SAPO-34) was added to 30 cc of this aqueous solution of ferric sulfate to impregnate the zeolite with the aqueous solution of ferric sulfate. This solution was filtrated, and then the collected product was dried and solidified with heating using a hot water bath.

Further, the dried product was heated in a muffle furnace at 300° C. for 3 hours to subject to the reactions as described below in Examples. The heated product had 6% by weight of a supported iron compound, calculated as $Fe_2O_3$.

PREPARATION EXAMPLE 5

$AgNO_3$ (0.88 g) was dissolved in 30 cc of an ion exchange water, giving an aqueous solution of silver nitrate. 10 g of a commercially available Si—Al—P zeolite (SAPO-34) was added to 30 cc of this aqueous solution of silver nitrate to impregnate the zeolite with the aqueous solution of silver nitrate. This solution was filtrated, and then the collected product was dried and solidified with heating using a hot water bath.

Further, the dried product was heated in a muffle furnace at 300° C. for 3 hours to subject to the reactions as described below in Examples. The heated product had 6% by weight of a supported silver compound, calculated as $Ag_2O$.

PREPARATION EXAMPLE 6

$HgSO_4$ (0.85 g) was dissolved in 30 cc of an ion exchange water, giving a aqueous solution of mercuric sulfate. 10 g of a commercially available Si—Al—P zeolite (SAPO-11) was added to 30 cc of this aqueous solution of mercuric sulfate to impregnate the zeolite with the aqueous solution of mercuric sulfate. This solution was filtrated, and then the collected product was dried and solidified with heating using a hot water bath. Further, the dried product was heated in a muffle furnace at 300° C. for 3 hours to subject to the reactions as described below in Examples. The heated product had 6% by weight of a supported mercury compound, calculated as HgO.

PREPARATION EXAMPLE 7

$CuSO_4 \cdot 5H_2O$ (1.88 g) and $AgNO_3$ (0.09 g) were dissolved in 30 cc of an ion exchange water, giving a aqueous solution. 10 g of a commercially available Si—Al—P zeolite (SAPO-11) was added to 30 cc of this aqueous solution to impregnate the zeolite with the aqueous solution. This solution was filtrated, and then the collected product was dried and solidified with heating using a hot water bath. Further, the dried product was heated in a muffle furnace at 300° C. for 3 hours to subject to the reactions as described below in Examples. The heated product had 6% by weight of a supported copper compound and 0.6% by weight of a supported silver compound, calculated as CuO and $Ag_2O$, respectively.

PREPARATION EXAMPLE 8

$CuSO_4 \cdot 5H_2O$ (1.88 g) and $AgNO_3$ (0.01 g) were dissolved in 30 cc of an ion exchange water, giving an aqueous solution. 10 g of a commercially available Si—Al—P zeolite (SAPO-11) was added to 30 cc of this aqueous solution to impregnate the zeolite with the aqueous solution. This solution was filtrated, and then the collected product was dried and solidified with heating using a hot water bath. Further, the dried product was heated in a muffle furnace at 300° C. for 3 hours to subject to the reactions as described below in Examples. The heated product had 6% by weight of a supported copper compound and 0.06% by weight of a supported silver compound, calculated as CuO and $Ag_2O$, respectively.

PREPARATION EXAMPLE 9

Pd(NO$_3$)$_2$ (1.13 g) was dissolved in 30 cc of an ion exchange water, giving an aqueous solution of palladium nitrate. 10 g of a commercially available Si—Al—P zeolite (SAPO-11) was added to 30 cc of this aqueous solution of palladium nitrate to impregnate the zeolite with the aqueous solution of palladium nitrate. This solution was filtered, and then the collected product was dried and solidified with heating using a hot water bath. Further, the dried product was heated in a muffle furnace at 300° C. for 3 hours to subject to the reactions as described below in Examples. The heated product had 6% by weight of a supported palladium compound, calculated as PdO.

PREPARATION EXAMPLE 10

CuSO$_4$.5H$_2$O (1.88 g) was dissolved in 30 cc of an ion exchange water, giving an aqueous solution of copper sulfate. 10 g of a commercially available high silica zeolite (manufactured by TOSOH CORPORATION) was added to 30 cc of this aqueous solution of copper sulfate to impregnate the zeolite with the aqueous solution. This solution was filtered, and then the collected product was dried and solidified with heating using a hot water bath. Further, the dried product was heated in a muffle furnace at 300° C. for 3 hours to subject to the reactions as described below in Examples. The heated product had 6% by weight of a supported copper compound, calculated as CuO.

PREPARATION EXAMPLE 11

CuSO$_4$.5H$_2$O (1.88 g) was dissolved in 30 cc of an ion exchange water, giving an aqueous solution of copper sulfate. 10 g of a commercially available aluminum phosphate (AlPO$_4$) was added to 30 cc of this aqueous solution of copper sulfate to impregnate this with the aqueous solution. This solution was filtered, and then the collected product was dried and solidified with heating using a hot water bath. Further, the dried product was heated in a muffle furnace at 300° C. for 3 hours to subject to the reactions as described below in Examples. The heated product had 4% by weight of a supported copper compound, calculated as CuO.

EXAMPLE 1

The catalyst of Preparation Example 1 (10 g) was placed in a stainless-steel reaction tube having an inside diameter of 10 mm and length of 250 mm, and was heated to 275° C. with a heater. CF$_3$CF$_2$ (CF$_2$CF$_2$)$_2$CH$_2$CH$_2$I and water were introduced into a vaporizer (preheat phase) at a rate of 2.5 g/hr and 12 g/hr, respectively, with a plunger pump and were vaporized. Air was introduced into the reaction tube as a carrier gas at a rate of 35 cc/min. The vaporized gases were carried to the catalyst by the air to cause a catalytic reaction on the catalyst. Reaction products were recovered with an ice trap and a dry ice/methanol trap provided at the outlet of the reaction tube. The analysis of the products by gas chromatography revealed that an alcohol (CF$_3$CF$_2$ (CF$_2$CF$_2$)$_2$CH$_2$CH$_2$OH) was formed at the degree of conversion of 98% and selectivity of 95%.

EXAMPLES 2 to EXAMPLE 4

Reactions were conducted in a manner similar to Example 1 using the catalysts of the above Preparation Examples 2 to 4. The results of analysis are shown in the table below.

|  | Example 2 | Example 3 | Example 4 |
| --- | --- | --- | --- |
| Kind of catalyst | Preparation Example 2 | Preparation Example 3 | Preparation Example 4 |
| Degree of conversion (%) | 97 | 34 | 48 |
| Selectivity (%) | 89 | 91 | 62 |

EXAMPLE 5

The catalyst of Preparation Example 5 (10 g) was placed in a stainless-steel reaction tube having an inside diameter of 10 mm and length of 250 mm, and was heated to 165° C. with a heater. In a manner similar to Example 1, CF$_3$CF$_2$(CF$_2$CF$_2$)$_2$CH$_2$CH$_2$I and water were supplied to the catalyst at a rate of 2.5 g/hr and 12 g/hr, respectively, to cause a catalytic reaction on the catalyst. Reaction products were recovered with an ice trap and dry ice/methanol trap provided at the outlet of the reaction tube. The GC analysis of the products revealed that an alcohol (CF$_3$CF$_2$ (CF$_2$CF$_2$)$_2$CH$_2$ CH$_2$OH) was formed at the degree of conversion of 100% and selectivity of 81%.

EXAMPLE 6

The catalyst of Preparation Example 6 (15 g) was placed in a stainless-steel reaction tube having an inside diameter of 10 mm and length of 250 mm, and was heated to 180° C. with a heater. CF$_3$CF$_2$ (CF$_2$CF$_2$)$_2$CH$_2$CH$_2$I and water were introduced into a vaporizer at a rate of 2.5 g/hr and 12 g/hr, respectively, and were vaporized. Air was introduced into the reaction tube as a carrier gas at a rate of 35 cc/min. The vaporized gases were carried to the catalyst in the above reaction tube by the air to cause a catalytic reaction on the catalyst. Reaction products were recovered with an ice trap and a dry ice/methanol trap provided at the outlet of the reaction tube. The GC analysis of the products revealed that an alcohol was formed at the degree of conversion of 93% and selectivity of 95%.

EXAMPLE 7 to EXAMPLE 11

Reactions were conducted using the catalysts of the above Preparation Examples 7 to 11 in a manner similar to Example 6 except with a different reaction temperature. The analysis results of the reaction products are shown in the table below.

|  | Example | | | | |
| --- | --- | --- | --- | --- | --- |
|  | 7 | 8 | 9 | 10 | 11 |
| Kind of catalyst | Prep. Ex. 7 | Prep. Ex. 8 | Prep. Ex. 9 | Prep. Ex. 10 | Prep. Ex. 11 |
| Reaction temperature (° C.) | 210 | 250 | 180 | 270 | 270 |
| Degree of conversion (%) | 100 | 95 | 78 | 64 | 4 |
| Selectivity (%) | 98 | 98 | 64 | 10 | 92 |

EXAMPLE 12

The catalyst of Preparation Example 8 (20 g) was placed in a stainless-steel reaction tube having an inner diameter of 10 mm and length of 250 mm, and was heated to 180° C. with a heater. $CF_3CF_2(CF_2CF_2)_pCH_2CH_2I$ (mixture having a molar ratio of constituents of p=1/p=2/p=3/p=4/p=5/p=6= 1.0/9.3/2.7/1.1/0.48/0.17) and water were introduced into a vaporizer at a rate of 2.8 g/hr and 12 g/hr, respectively, and were vaporized. Air was introduced into the reaction tube as a carrier gas at a rate of 35 cc/min. The vaporized gases were carried to the catalyst in the above reaction tube by the air to cause a catalytic reaction on the catalyst. Reaction products were recovered with an ice trap and a dry ice/methanol trap provided at the outlet of the reaction tube. The GC analysis of the products revealed that the corresponding alcohols were formed at the degree of conversion of 91% and selectivity of 91%.

EXAMPLE 13

A reaction was conducted in a manner similar to Example 1 for about 400 hours continuously, and reaction products were recovered. The GC analysis of the reaction products revealed that an alcohol was formed at the degree of conversion of 90% and selectivity of 95%.

EXAMPLE 14

Using the method of Example 6, the reaction was conducted under increased pressure (0.392 MPa (absolute pressure)). The reaction yielded an alcohol at the degree of conversion of 100% and selectivity of 98%.

EXAMPLE 15

The reaction product obtained in Example 13 was filtrated with heating at 80° C., giving solid $I_2$ at a rate of recovery of 60%.

What is claimed is:

1. A method for preparing a fluorine-containing alcohol compound represented by formula (II):

$$Rf—(CH_2)_nOH \quad (II)$$

wherein Rf represents a perfluoroalkyl group or a polyfluoroalkyl group and n is an integer from 1 to 5, the method comprising the step of reacting water with a halogenated fluorine compound represented by formula (I):

$$Rf—(CH_2)_nX \quad (I)$$

wherein Rf is as defined in the above, X represents I, Br or Cl and n is as defined in the above, in the presence of a catalyst having at least one component selected from,
(i) at least one element selected from the elements in Group 1B, Group 2B, and Group 7A of the periodic table,
(ii) at least one ion of the element of the above (i),
(iii) at least one oxide containing one or more elements of the above (i),
(iv) at least one hydroxide containing one or more elements of the above (i), and
(v) at least one salt containing one or more elements of the above (i), said component being supported on at least one complex oxide selected from Si—Al complex oxides, Al—P complex oxides and Si—Al—P complex oxides, and said complex oxide being an oxide having a zeolite structure and in the absence of an organic solvent.

2. The method according to claim 1, wherein the reaction between the halogenated fluorine compound and water is carried out in an atmosphere of an oxygen-containing gas.

3. The method according to claim 1, wherein the reaction is carried out under increased pressure.

4. The method for preparing a fluorine-containing alcohol compound according to claim 2, wherein X in formula (I) is I, the method further comprising the step of recovering $I_2$ produced as a byproduct.

* * * * *